United States Patent [19]

McCague

[11] Patent Number: 4,839,155

[45] Date of Patent: Jun. 13, 1989

[54] IODOTAMOXIFEN DERIVATIVES AND USE FOR ESTROGEN RECEPTOR-POSITIVE BREAST CANCER DETECTION AND THERAPY

[75] Inventor: Raymond McCague, Reigate, England

[73] Assignee: National Research Development Corporation, United Kingdom

[21] Appl. No.: 94,507

[22] Filed: Sep. 9, 1987

[30] Foreign Application Priority Data

Sep. 11, 1986 [GB] United Kingdom ............... 8621908
May 19, 1987 [GB] United Kingdom ............... 8711790

[51] Int. Cl.[4] .................. A61K 49/02; C07D 207/04; C07C 93/06
[52] U.S. Cl. .................. 424/1.1; 564/324; 548/575; 514/428; 514/651; 514/239.2; 514/317; 514/648; 544/174; 546/236
[58] Field of Search .................. 546/236; 564/324; 544/174; 424/1.1; 514/428, 651, 648, 317, 239.2; 548/575

[56] References Cited

U.S. PATENT DOCUMENTS 3,288,806 11/1966 Dewald .................. 564/324

OTHER PUBLICATIONS

Lieberman et al., "Inhibition of Estradiol-Stumulated Prolactin Synthesis", J. Biol. Chem., 1983, 258(8), 4734–40, [Chemical Abstracts, vol. 99, 1983, p. 77].
Sham et al., "Fluorotamoxifen", J. Med. Chem., 1985, 28(10), 1504–11, [Chemical Abstracts, vol. 103, 1985, p. 341].
K. E. Allen et al., British Journal of Pharmacology, 71, 83–91 (1980).
W. D. Bloomer et al., Int. J. Radiat. Biol., 38, 197–202 (1980).
G. L. Tonnensen et al., Int. J. Radiat. Isot., 32, 171–173 (1981).
D. H. Hunter et al., Can. J. Chem., 61, 421–426 (1983).
D. H. Hunter et al., Appl. Radiat. Isot., 37, 889–891 (1986).
D. W. Robertson et al., J. Med. Chem., 25, 167–171 (1982).
M. M. King et al., Journal of National Cancer Institute, 74, 447–451 (1985).
L. Maddedu et al., Anticancer Research, 6, 11–16 (1986).
G. Leclercq et al., J. Steroid. Biochem., 19, 75–85 (1983).
A. B. Foster et al., J. Med. Chem., 28, 1491–1497 (1985).

Primary Examiner—John S. Maples
Attorney, Agent, or Firm—Jacobs & Jacobs

[57] ABSTRACT

Iodotamoxifen derivatives which are compounds of formula (3)

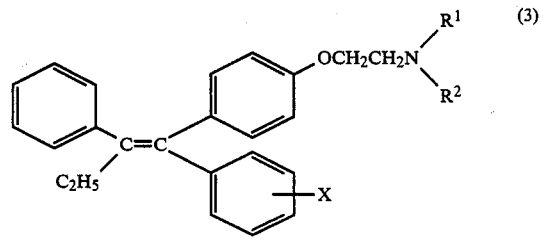

wherein X represents 3- or 4- iodo and $R^1$ and $R^2$, which may be the same or different, represent $C_{1-3}$ alkyl, especially methyl or ethyl, groups or $R^1$ represents a hydrogen atom and $R^2$ a $C_{1-3}$ alkyl group or $R^1$ and $R^2$ together with the nitrogen atom to which they are attached represent a saturated heterocyclic group, especially a pyrrolidino, piperidino, 4-methylpiperidino or morpholino group, and their pharmaceutically acceptable acid addition salts are potent anti-estrogenic compounds useful for treatment of estrogen receptor-positive (hormone-dependent) breast cancers.

Radioisotopic iodotamoxifen derivatives of formula (3) are useful in radiotherapy or gamma ray imaging of these cancers.

10 Claims, No Drawings

IODOTAMOXIFEN DERIVATIVES AND USE FOR ESTROGEN RECEPTOR-POSITIVE BREAST CANCER DETECTION AND THERAPY

BACKGROUND OF THE INVENTION

1. Field of the invention

This invention relates to derivatives of tamoxifen, their preparation and use in therapy and diagnosis of breast cancer.

2. Description of prior art

Tamoxifen is Z (1,2-diphenyl)-1-[4-(2-dimethylaminoethoxy)-phenyl]-1-butene of formula (1)

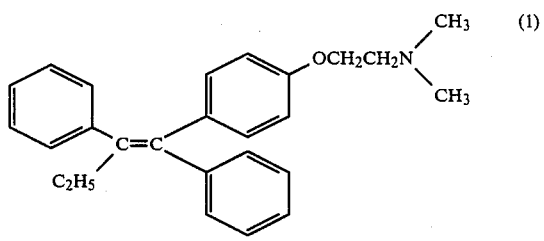

Its anti-estrogenic properties have led since 1971 to its clinical use in the treatment of malignant tumors, especially estrogen receptor-positive (hormone-dependent) breast cancer.

Tamoxifen has a relatively low affinity for the estrogen receptor (ER). Attempts have therefore been made to find tamoxifen derivatives having improved ER affinity. Changes have been made in virtually every part of the molecule. One derivative which at first seemed promising was the 4-hydroxy derivative of formulat (2)

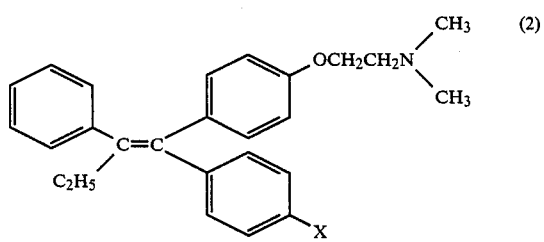

in which X=—OH. This compound was shown by in vitro tests to be a potent anti-estrogen, but unfortunately proved in vivo to be less effective than tamoxifen, owing to rapid glucuronidation of the hydroxyl group followed by excretion.

Several derivatives of tamoxifen are known which have other 4-position substituents, in which X is methoxy, methyl, fluoro or chloro. These compounds have been evaluated by K. E. Allen et al., British Journal of Pharmacology 71, 83–91 (1980). The methyl, chloro and fluoro derivatives were of particular interest as they are unlikely to be metabolised to the 4-hydroxy derivative and thence glucuronidated. An in vitro test of estrogen receptor affinity indicated that tamoxifen was approximately equiactive with its 4-methyl, fluoro- and chloro-derivatives. In vivo rat uterine weight tests indicated that these derivatives has lower anti-estrogenic activity than tamoxifen. Other tests indicated that the activity of the 4-methoxy derivative was about the same as tamoxifen.

SUMMARY OF THE INVENTION

It has now been found that the 4-iodo derivative (formula 2: X=iodo) has greater potency than tamoxifen in relation to estrogen receptor-positive breast cancer. In view of the report by K. E. Allen et al., supra, that the 4-fluoro and 4-chloro compounds are (at best) of no greater potency than tamoxifen, the present finding is most surprising. Also, the 4-bromo, 3-iodo and 3-bromo analogues show promise as alternatives to tamoxifen of at least equal potency.

These tamoxifen derivatives, which are named E 1-[4-(2-dimethylaminoethoxy)phenyl]-1-(3- and 4-iodophenyl)-2-phenyl-1-butene and E 1-[4-(2-dimethylaminoethoxy)phenyl]-1-(3- and 4-bromophenyl)-2-phenyl-1-butene, are believed to be new compounds. Analogues thereof in which the dimethylamino group is replaced by other dialkylamino groups or by monoalkylamino groups or a nitrogen-containing saturated heterocyclic ring are also believed to be novel and are potent against ER-positive breast cancer. Accordingly, the present invention provides 3- and 4-iodo and -bromotamoxifen derivatives which are compounds of formula (3)

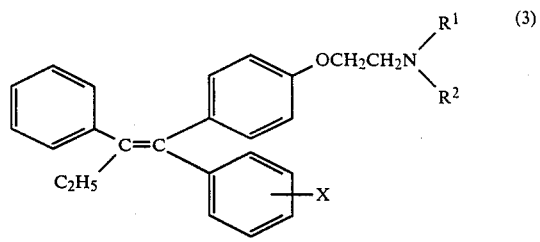

wherein X represents 3- or 4- iodo or bromo and the $R^1$ and $R^2$ symbols, which may be the same or different, represent $C_{1-3}$ alkyl, especially methyl or ethyl, groups or $R^1$ represents a hydrogen atom and $R^2$ a $C_{1-3}$ alkyl group or $R^1$ and $R^2$ together with the nitrogen atom to which they are attached represent a saturated heterocyclic group, typically having 5 or 6 ring atoms, especially a pyrrolidino, piperidino, 4-methylpiperidino or morpholino group, and their pharmaceutically acceptable acid addition salts.

The invention further includes:

the 3- and 4-iodo and -bromotamotamoxifen derivatives, i.e. the compounds of formula (3) and their pharmaceutically acceptable addition salts for use in treatment of ER-positive breast cancer;

the 3- and 4-iodo and -bromotamoxifen derivatives for use in the preparation of a medicament for treatment of ER-positive breast cancer or, where national patent law permits, a method of treating such a cancer in a human patient which comprises administering to the patient a therapeutically effective amount of the tamoxifen derivative;

a pharmaceutical composition comprising a 3- or 4-iodo or -bromotamoxifen derivative in association with a pharmaceutically effective diluent, carrier or excipient;

a process for the preparation of the 3- and 4-iodo and -bromotamoxifen derivatives which comprises reacting 1-[4-(2-chloroethoxy)phenyl]-2-phenyl-1-butene with an organometallic reagent derived from 1,3- or 1,4-diiodo- or -dibromobenzene and capable of addition to a ketone group, in a substantially anhydrous organic solvent, to form a tertiary alcohol, dehydrating the tertiary alcohol to eliminate a molecule of water and thereby form 1-[4-(2-chloroethoxy)-phenyl]-1-(3- or 4-iodophenyl or -bromophenyl)-2-phenyl-1-butene as an isomeric mixture, separating the E isomer and reacting the E isomer with an amine of formula NR$^1$R$^2$, R$^1$ and R$^2$ being defined as above; and a process for the preparation of the 3- and 4-iodo and -bromo tamoxifen derivatives which comprises reacting a ketone of formula (4)

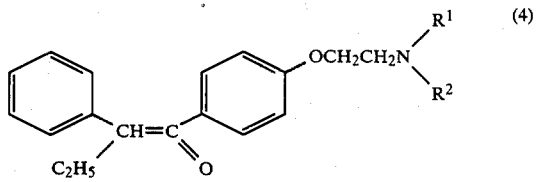

R$^1$ and R$^2$ beind defined as above, in one step with an organometallic reagent as defined above, in a substantially anhydous orgaic solvent, to form a tertiary alcohol, dehydrating the tertiary alcohol to eliminate a molecule of water and thereby form 1-[4-(2-NR$^1$R$^2$-substituted ethoxy)phenyl]-1-(3- or 4-iodophenyl or 4-bromophenyl)-2-phenyl-1-butene as an isomeric mixture, and separating the E isomer.

The iodotamoxifen derivatives of the invention include per se those wherein the iodine atoms comprise radioisotopic iodine atoms. Predominantly useful such atoms are $^{125}$I for radiotherapy of estrogen receptor-positive breast cancers and $^{131}$I and $^{123}$I which are gamma-emitters and therefore useful in imaging the tumours. These compounds, for such uses as well as per se, are part of the invention.

The radioisotopic iodotamoxifen derivatives can be prepared by a process comprising reacting a compound of formula

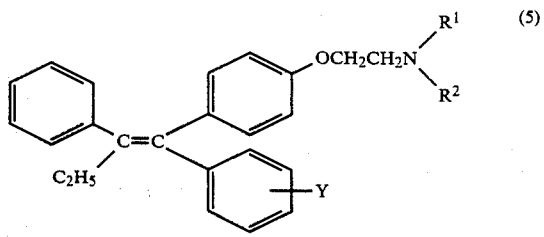

wherein R$^1$ and R$^2$ are as defined in connction with formula (3) and Y represents a 3- or 4-substituent, whether an atom or a group, capable of being cleaved from its benzene ring (including within this definition a non-radioisotopic iodine atom), with a reagent capable of effecting such cleavage and with a source of radioisotopic iodine (which can be added as molecular iodine or iodide ions according to the cleavage-effecting reagent used and other reaction conditions). Preferably Y is chloro, bromo, iodo or amino.

DESCRIPTION OF THE PREFERRED EMBODIMENTS

The iodo derivatives are preferred to the bromo, and the 4-iodo to the 3-iodo. Preferably R$^1$ and R$^2$ are both alkyl groups, most preferably methyl, or NR$^1$R$^2$ is pyrrolidino.

The compounds of formula (3) and their salts are prepared starting from ketones which are known compounds. The preferred reagent for the preparation of the organometallic halobenzene species is n-butyllithium. Alternatively the magnesium Grignard reagent can be used. The immediate product of the organometallic reaction is a tertiary alcohol which is then dehydrated to eliminate a molecule of water and thereby provide the ethylenic double bond required. The dehydration is preferably carried out by heating the alcohol in a strong acid such as concentrated hydrochloric acid. A mixture of isomers is produced of which the desired one is that in which the ethyl group and the (2-aminoethoxy)phenyl group are trans. The Z/E nomenclature designates this as Z for tamoxifen itself and E for the iodo or bromo derivatives.

In one embodiment of the invention, the starting ketone already contains the (2-aminoethoxy)phenyl group and therefore the reaction can be carried out in one step (since the tertiary alcohol need not be isolated). The isomer separation is then carried out on the end product.

Alternatively, the starting ketone contains the (2-chloroethoxy)phenyl group. The dehydration to the olefin yields the (2-chloroethoxy)phenyl intermediate. The isomers can be separated by crystallisation, which is very convenient, and the desired E isomer appropriately aminated by reaction with the alkylamine or heterocyclic amine required. The amination can be carried out in any manner known in the synthesis of tamoxifen, for example heating the chloroethoxy intermediate with the amine in a sealed vessel.

The acid addition salts can be prepared in any manner analogous to those of taoxifen, at any appropriate stage of the overall synthesis after formation of the tertiary alcohol. Usually they will be prepared as the final stage. Examples of such salts are the hydrochloride, sulphate, phosphate, acetate and citrate. In the "direct" method of preparation of the iodo or bromotamoxifen derivatives, an acid addition salt is formed under the acidic dehydration conditions used. This will ordinarily be neutralised with, say, sodium hydroxide. The isomers can then be separated either as the free bases or, after adding a approximately stoichiometric proportion of acid, as acid addition salts.

For pharmaceutical formulation, the iodo and bromotamoxifen derivatives can be formulated in the same or a similar way to tamoxifen and administered similarly and in about the same dose. Preferably they are formulated as tablets.

The iodotamoxifen derivatives include those wherein the iodine atoms in some or all of the molecules of a given sample have a radioisotopic (a radioactive or "hot") iodine atom. Predominantly useful such atoms are $^{125}$I which emits low energy electrons having a short, sub-cellular range and $^{131}$I and $^{123}$I which emit gamma rays. The $^{125}$I isotopic iodine is useful in the therapy of tumour cels containing oestrogen receptors, in the same manner as has already been reported for another $^{125}$I tamoxifen derivative in which the iodine atom is attached to the same benzene ring as the 2-dimethylaminoethoxy group, in the ortho position thereto, see W. D. Bloomer et al., Int. J. Radiat. Biol, 38, 197–202 (1980). The $^{123}$I and $^{131}$I isotopes, of which $^{131}$I is preferred, are gamma emitters and therefore usable for imaging of oestrogen receptor-carrying tumour cells. The use of all these three isotopes in another iodotamoxifen, namely that in which the iodine atom is present in the "diagonally opposite" position to that of formula (3), that is to say is para in the benzene ring attached to the carbon atom to which the ethyl group is also attached, is suggested by D. H. Hunter et al., Can. J. Chem. 61, 421–426 (1983). The content of radioisotopic iodine in the iodotamoxifen formulation should be adjusted to conform to conventional radiotherapy and imaging practice.

The commonly used radioisotopes of iodine have a short half-life, for $^{131}$I 8 days, for $^{125}$I 60 days, and for $^{123}$I 13 hours. It is therefore necessary to prepare the radioisotopic compounds of the invention only shortly before the expected time of use. One suitable method of preparation, referred to above, starts from the corresponding compound substituted by non-radioactive ("cold") X (X=bromo or iodo) or by some other atom or group, for example chloro or amino, capable of undergoing a reaction in which the cold X or other atom or group is pulled off or cleaved from the benzene ring of the tamoxifen molecule.

In one aspect the starting compound is the "cold" iodotamoxifen, which is reacted with a copper (I) or (II) salt and an appropriate source of "hot" (radioisotopic) iodide such as sodium iodide. This a modified version of the Rosenmund-von Braun reaction in which an aryl iodide is convertible to the aryl cyanide by the action of copper (I) cyanide. Since this method does not give an iodotamoxifen product having a high proportion of its iodine atoms in radioisotopic form, it is not well suited to the production of iodotamoxifen for imaging purposes.

Another embodiment comprises reacting the starting compound containing the "cold" X with an alkyllithium and "hot" molecular iodine, in an inert atmosphere. The reaction mechanism is illustrated below using bromine as the cleavable atom and t-butyl lithium as the reagent which effects the cleavage. Ar denotes the residue of the tamoxifen molecule.

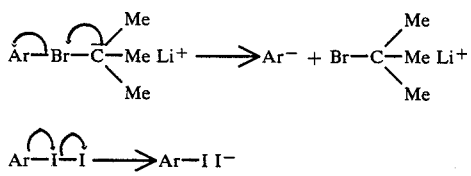

Other alkyllithium reagents could be used in place of t-butyl lithium. The reaction takes place in a non-oxidising atmosphere in order to avoid production of a hydroxytamoxifen and a reducing atmosphere such as would react with molecular iodine is also to be avoided. An inert atmosphere is therefore the most suitable.

The reaction temperature can be any appropriate to the reaction equilibrium but is usually in the range of −80° to +20° C. A solvent is normally required and can be any appropriate to the temperature. Tetrahydrofuran is preferred at low temperatures. The iodine should be added in stoichiometric excess for the reaction. Preferably the radioisotopic iodine is added portionwise, less than the stoichiometric amount being added initially, whereby up to half of the radioisotopic I$_2$ molecules added will become incorporated in the tamoxifen molecule. Addition of the remainder of the iodine, to a stoichiometric excess in total, as "cold" iodine will ensure that there is no avoidable wastage of the radioisotope. Of course, some of it (theoretically a half) will be wasted as iodide ions, which, however, can be recovered by methods known to those skilled in the raadioisotope art.

It will be seen that the 4-bromotamoxifen derivatives of formula (3) are useful as intermediates in the preparation of radioisotopic 4-iodotamoxifen derivatives. When a 4-chlorotamoxifen is used as the starting compound, it can be prepared analogously to the 4-bromotamoxifen derivatives described herein. The amino group of the 4-amino analogue can be cleaved and iodine substituted by the action of hyponitrous acid and radiolabelled sodium iodide.

Another method proceeds via a tributyltin intermediate, which can be stored and then converted to the iodotamoxifen immediately before use. This intermediate can be prepared by reacting the 4-bromo- or iodotamoxifen derivative with n-butyllithium (as described above) and then with tributyl tin chloride. This method has been described by W. D. Bloomer et al., supra.

Other methods of introducing a radioactive iodine atom will be found in R. H. Seevers and R. E. Counsel, Chem. Rev. 82, 575–590 (1982) and such methods are usable mutatis mutandis in the context of the present invention.

The following Examples illustrate the invention. Examples 1–6 illustrate preparation of iodo and bromotamoxifen derivatives. "Ether" means diethyl ether. Examples 7 and 8 indicate antiestrogenic effects of the derivatives and Example 9 a pharmaceutical composition. Examples 10 and 11 illustrate preparation of radioisotopic iodotamoxifen derivatives.

EXAMPLE 1

Preparation of E 1-[4-(2-dimethylaminoethoxy)phenyl]-1-(4-iodophenyl)-2-phenyl-1-butene ("4-iodotamoxifen")

A stirred solution of 1,4-diiodobenzene (4.21 g, 12.7 mmol) in dry tetrahydrofuran (20 ml) was cooled under nitrogen by a dry ice-acetone bath. n-Butyllithium (8.5 ml of a 1.55M solution in hexane, 12.7 mmol) was added. After 5 minutes, a solution of 1-[4-(2-dimethylaminoethoxy)phenyl]-2-phenyl-1-butanone (2.0 g, 6.4 mmol) was added and the mixture allowed to warm to room temperature. After 15 hours, the mixture was poured into water (60 ml) and extracted with ether (2×50 ml). The ether extracts were concentrated and the residual oil dissolved in ethanol (20 ml). Concentrated hydrochloric acid (10 ml) was added and the mixture heated under reflux for 4 hours, then cooled, and poured into water (100 ml). The solution was basified with aqueous sodium hydroxide (3M) and extracted with ether (100 ml). The ether extract was dried with sodium sulphate, concentrated, and the residue applied to a column of silica (Merck 15111, 80 g). Elution with 1:1 light petroleum (b.p. 40°-60° C.-ether containing an increasing proportion of triethylamine gave after a forerun of tamoxifen which was discarded, at 5% triethylamine, a mixture of 4-iodotamoxifen and its Z isomer:-

(i) 241 mg consisting of 3:1 trans (E):cis (Z) isomers
(ii) 363 mg consisting of 1:1 trans (E):cis (Z) isomers
(iii) 406.5 mg consisting of 1:2 trans (E):cis as determined by NMR

| -continued |
| --- |
| (Z) isomers |

The total yield of products was 1.01 g (32%).

Recrystallisation of band (i) above gave a sample of the title compound, pure trans (E) isomer, m.p. 112°–114° C. (from light petroleum, b.p. 40°–60° C.). Found C, 62.88; H, 5.72; N, 2.79; I, 25.30%. $C_{26}H_{28}INO$ requires C, 62.78; H, 5.67; N, 2.82; I, 25.51% NMR: $\delta_H$(CDCl$_3$, 250 MHz) 0.91 (3H, t J 7.4 Hz, CH$_3$CH$_2$), 2.28 (6 H, s, NMe$_2$), 2.43 (2H, q, J 7.4 Hz, CH$_3$CH$_2$), 2.64 (2H, t, J 5.8 Hz, OCH$_2$CH$_2$N), 3.92 (2H, t, J 5.8 Hz, OCH$_2$CH$_2$N), 6.55 (2H, d, J 8.8 Hz, H-3,5 of C-C$_6$H$_4$-0), 6.73 (2H, d, J 8.8 Hz, H-2,6 of C-C$_6$H$_4$-0), 6.98 (2H, d, J 8.3 Hz, H-2,6 of C-C$_6$H$_4$-I), 7.04–7.22 (5H, m, Ph), 7.66 (2H, d, J 8.3 Hz, H-3,5 of C-C$_6$H$_4$-I); mass spectrum m/z 497 (M$^+$, 36%), 380(3), 72(100), 58(100).

The cis (Z) isomer gave $\delta_H$ (CDCl$_3$, 60 MHz) inter alia 2.32 (6H, s, NMe$_2$), 4.07 (2H, t, J 6 Hz, OCH$_2$CH$_2$N).

EXAMPLE 2

Preparation of E
1-[4-(2-dimethylaminoethoxy)phenyl]-1-(4-bromo phenyl)-2-phenyl-1-butene ("4-bromotamoxifen")

A stirred solution of 1,4-dibromobenzene (6.88 g, 29.15 mmol) in dry tetrahydrofuran (30 ml) was cooled under nitrogen by a dry ice-acetone bath and n-butyllithium (15.1 ml of a 1.55M solution in hexane; 24 mmol) added over 2 minutes. A precipitate formed. After 10 minutes, a solution of 1-[4-(2-dimethylaminoethoxy)-phenyl]-2-phenyl-1-butanone (6.09 g, 19.43 mmol) in tetrahydrofuran (15 ml) was added and the mixture allowed to warm to room temperature.

After 16 hours, the mixture was worked up as described above for 4-iodotamoxifen to give crude tertiary alcohol as a solid, which was dissolved in ethanol (100 ml). Concentrated hydrochloric acid (60 ml) was added and the mixture heated up under reflux for 20 hours. Work up was as described above for 4-iodotamoxifen. The crude product was dissolved in hot light petroleum (b.p. 80°–100° C.) (40 ml). Cooling gave crystals of the title compound, i.e. the trans (E) isomer, (2.78 g, 32% yield). The mother liquors were applied to a column of silica (60 g). Elution with 20:20:1 light petroleum (b.p. 40°–60° C.)-ether-triethylamine gave (i) 4.36 g oil consisting of 2.5:1 Z:E isomers
(ii) 0.58 g oil consisting of 4:1 Z:E isomers The total yield was 7.72 g, 88%. The proportion of isomers in the crude product was estimated as 1.2:1.

Recrystallisation of (i) gave further trans (E) isomer, 0.19 g, then cis (Z) isomer, 1.10 g.

In a repeat of this reaction, but using a milder dehydration procedure (25 ml conc. HCl, 200 ml ethanol, reflux 30 minutes) the ratio of isomers in the crude product was improved to 1.6:1 but the yield was lower, 72% (35% yield of trans (E) isomer isolated following crystallisation).

The trans (E) isomer, 4-bromotamoxifen, had m.p. 114°–116° C. (from light petroleum, b.p. 80°–100° C.). Found C, 69.44; H, 6.29; N, 2.92; Br, 17.88. $C_{26}H_{28}BrNO$ requires C, 69.32; H, 6.26; N, 3.11; Br, 17.74%; NMR: $\delta_H$(CDCl$_3$, 250 MHz) 0.91 (3H, t, J 7.4 Hz, CH$_3$CH$_2$), 2.28 (6H, s, NMe$_2$), 2.44 (2H, q, J 7.4 Hz, CH$_3$CH$_2$), 2.64 (2H, t, J 5.7 Hz, OCH$_2$CH$_2$N), 3.92 (2H, t, J 5.7 Hz, OCH$_2$CH$_2$N), 6.56 (2H, d J 8.8 Hz, ArH ortho to OR), 6.73 (2H, d, J 8.8 Hz, ArH meta to OR), 7.08–7.26 (7H, m, ArH), 7.46 (2H, d, J 8.3 Hz, ArH ortho to Br).

The cis (Z) isomer had m.p. 77°–78° C. (from light petroleum, b.p. 80°–100° C.). Found C, 69.49; H, 6.31; N, 3.05; Br, 17.70. $C_{26}H_{28}BrNO$ requires C, 69.33; H, 6.27; N, 3.11; Br, 17.74%; $\delta_H$(CDCl$_3$, 60 MHz), 0.90 (3H, t, J 7 Hz, CH$_3$CH$_2$), 2.31 (6H, s, NMe$_2$), 2.48 (2H, q, J 7 Hz, CH$_3$CH$_2$), 2.71 (2H, t, J 6 Hz, OCH$_2$CH$_2$-NMe$_2$), 4.06 (2H, t, J 6 Hz, OCH$_2$CH$_2$NMe$_2$), 6.62 (2H, d, J 9 Hz, ArH ortho to OR), 6.9–7.3 (11H, m, ArH).

EXAMPLE 3

Preparation of 4-iodotamoxifen via the (2-chloroethoxy)phenyl intermediate

1-[4-(2-chloroethoxy)phenyl]-2-phenyl-1-butanone has been prepared by R. McCague, *J. Chem. Research*, 1986, (S), 58–9; (M), 771–93, by Friedel-Crafts condensation of 2-phenylbutanoic acid and (2-chloroethoxy)-benzene. 2-Phenylbutanoic acid is commercially available. (2-Chloroethoxy)benzene is obtainable by alkylation of phenol with 1,2-dichloroethane or by reaction of 2-phenoxyethanol with thionyl chloride.

A stirred solution of 1,41-diiodobenzene (21.8 g, 66 mmol) in dry tetrahydrofuran (100 ml) under nitrogen was cooled to ca.-75° C. and n-butyllithium (41.2 ml of a 1.6M solution in hexane, 66 mmol) introduced over 5 minutes. After 10 minutes, a solution of 1-[4-(2-chloroethoxy)phenyl]-2-phenyl-1-butanone (20.0 g, 66 mmol) in dry tetrahydrofuran (40 ml) was added and the mixture allowed to warm to room temperature. After 20 hours, the mixture was partitioned between water (200 ml) and ether (200 ml). The ether solution was concentrated and the residual oil dissolved in ethanol (300 ml). Concentrated hydrochloric acid (100 ml) was added, the mixture heated under reflux for 4 hours, then cooled and poured into water (300 ml). The products were extracted with ether (2×150 ml), the combined extracts washed with water (200 ml), dried with sodium sulphate and concentrated to give a brown oil which was dissolved in ethanol (200 ml). Crystals of mainly 1-[4-(2-chloroethoxy)phenyl]-1-(4-iodophenyl-2-phenyl-1-butene, i.e. the desired trans (E) isomer, of the (2-chloroethoxy)phenyl intermediate, were deposited, recrystallisation of which gave the pure isomer (12.92 g, 40%), m.p. 96°–97° C. Concentration of the original mother liquors gave the cis (Z) isomer (7.03 g, 22%), m.p. 110°–112° C.

Analysis of the crude oil by proton n.m.r. spectroscopy showed that it contained a 1.5:1 mixture of trans (E) and cis (Z) isomers.

A solution of E-1-[4-(2-chloroethoxy)phenyl]-1-(4-iodophenyl)-2-phenyl-1-butene (3.05 g) in 33% diethylamine in ethanol (60 ml) was boiled under reflux for 20 hours. The mixture was concentrated, a procedure made necessary only because of escape of the gaseous dimethylamine under these conditions, further 33% dimethylamine solution (60 ml) was added and reflux was continued for a further 20 hours. The mixture was again concentrated and the residue partitioned between ether (50 ml) and aqueous sodium hydroxide (1M; 50 ml). The ether solution was concentrated and the residue applied to a column of silica gel (Merck 15111, 40 g). Column chromatography was need to remove a small amount of unreacted starting material from the product which could not be removed by recrystallisation. This problem and the concentration step during addition of dimethylamine could have been overcome by carrying out the reaction in a sealed bomb. Elution with 5% methylamine in 1:1 ether-light petroleum (b.p. 40°–60° C.) gave 4-iodotamoxifen, which was further purified by recrystallisation from light petroleum (b.p. 40°–60° C.) (2.60 g, 84% yield), identical to that of Example 1.

EXAMPLE 4

Preparation of E-1-[4-(2-Diethylaminoethoxy)phenyl]-1-(4-iodophenyl)-2-phenyl-1-butene The method of Example 3 was used, replacing the dimethylamine addition by a single portion of 1:1 diethylamine-ethanol (v/v) and refluxing for 2 days. 1.069 g of the (2-chloroethoxy)phenyl compound gave 1.03 g (93%) of the title compound, m.p. 58°–59° C. Found: C, 64.10; N, 6.21; N, 2.63; I, 24.12. $C_{28}H_{32}INO$ requires C, 64.00; H, 6.14; N, 2.67; I, 24.15%.

EXAMPLE 5

Preparation of E-1-[4-(2-(N-pyrrolidino)ethoxy)phenyl]-1-(4-iodophenyl-2-phenyl-1-butene)

The chloroethoxy compound (1.748 g) prepared as in Example 3 and pyrrolidine (10 ml) in ethanol (30 ml) were heated under reflux for 2 hours. The mixture was then concentrated and partitioned between ether (30 ml) and aqueous sodium hydroxide (1M; 30 ml). The ether solution was concentrated and the title compound recrystallised from light petroleum (b.p. 80°–100° C.), yield 1.72 g, (92%), m.p. 108°–109° C. Found: C, 64.28; H, 5.83; N, 2.64; I, 24.06. $C_{28}H_{30}INO$ requires C, 64.25; H, 5.78; N, 2.68; I, 24.24%. (Owing to greater reactivity of pyrrolidine than dimethylamine or diethylamine, all the starting material was consumed rapidly and chromatography was not required).

EXAMPLE 6

Preparation of E 1-[4-(2-dimethylaminoethoxy)phenyl]-1-(3-iodophenyl)-2-phenyl-1-butene ("3-iodotamoxifen")

A stirred solution of 1,3-diiodobenzene (5.45 g, 16.5 mmol) in dry tetrahydrofuran (25 ml) at −78° C. under nitrogen was treated with a solution of n-butyl lithium in hexane (1.6M; 10.3 ml, 16.5 mmol). After 5 min, a solution of 1-[4-(2-chloroethoxy)-phenyl]-2-phenyl-1-butene (5.0 g, 16.5 mmol) in dry tetra-hydrofuran (15 ml) was added and the mixture allowed to warm to room temperature. After 20 h, the mixture was poured into water (100 ml) and the products extracted with ether (2×50 ml). The extracts were concentrated under vacuum and the residue dissolved in ethanol (80 ml). Concentrated hydrochloric acid (30 ml) was added and the mixture heated under reflux. After 4 h, the mixture was cooled and partitioned between water (100 ml) and ether (2×60 ml). The ether layers were dried with sodium sulphate, concentrated, and the residue chromatographed on silica gel (Merck 15111, 60 g). Elution with 1:20 dichloromethane-light petroleum (b.p. 60°–80° C.) gave 1-[4-(chloroethoxy) phenyl]-1-(3-iodophenyl)-2-phenyl-1-butene as a ca. 1.5:1 mixture of E (trans) and Z (cis) isomers (determined by n.m.r. spectroscopy) and as an oil (6.46 g, 80% yield). This mixture (3.63 g) was dissolved in a solution of methylamine (30% w/v) in ethanol, and the resulting solution heated in a sealed vessel at 100° C. for 4 h, then cooled and concentrated to dryness. The residue was partitioned between aqueous sodium hydroxide (100 ml) and ether (100 ml). The ether solution was washed with water (50 ml), dried with sodium sulphate and the residual oil dissolved in cyclohexane (10 ml). Eventually 3-iodotamoxifen crystallised (1.51 g, 41%), m.p. 55°–57° C. NMR: $\delta_H$ (CDCl$_3$, 250 MHz) 0.91 (3H, t, J 7.4 Hz, CH$_3$CH$_2$), 2.29 (3H, s, NMe$_2$), 2.43 (2H, q, J 7.4 Hz, CH$_3$CH$_2$), 2.65 (2H, t, J 5.8 Hz, OCH$_2$CH$_2$N), 3.93 (2H, t, J 5.8. Hz, OCH$_2$CH$_{2N}$), 6.57 (2H, d, J 8.8 Hz, ArH ortho to side chain), 6.74 (2H, d, J 8.8 Hz, ArH meta to side chain), 7.05–7.26 (7H, m, ArH), 7.58–7.63 (2H, m, ArH ortho to I).

EXAMPLE 7

Relative binding affinities (RBA) of 4-iodo and bromotamoxifen and also of tamoxifen and 4-hydroxytamoxifen for comparison were determined by a rat uterine cytosol test, as follows. Immature rat uterine cytosol was incubated at 18° C. for 30 minutes with $5\times 10^{-9}$M ($^3$H)estradiol in the absence and presence of increasing amounts ($10^{-9}$-$10^{-5}$M) of the test compound or unlabelled estradiol (control). Unbound compounds were then removed with dextran-coated charcoal, and the amounts of estrogen receptor-bound ($^3$H)estradiol were measured. The relative concentrations of estradiol and test compound required to achieve 50% inhibition of ($^3$H)estradiol binding are the RBA: RBA=([I$_{50}$](estradiol)/[I$_{50}$](test compound×100.

A whole cell assay was then performed using the MCF-7 human breast cancer cell line obtained from the Michigan Cancer Foundation, Detroit, USA. MCF-7 cells were maintained at 37° C. in monolayer culture in closed T-25 dishes in mininal essential medium (MEM) supplemented with L-glutamine (0.6 mg/ml), gentamycin (40 micrograms/ml). penicillin (100 U/ml) streptomycin (100 micrograms/ml) and 10% inactivated fetal calf serum (inactivated for 1 hour at 56° C.). The MCF-7 cells were incubated at 37° C. for 50 minutes with $10^{-9}$M ($^3$H)estradiol in the absence or presence of increasing amounts ($10^{-10}$-$10^{-5}$M) of the test compound or unlabelled estradiol (control). Bound compounds were then extracted with ethanol, and the amounts of estrogen receptor bound ($^3$H) estradiol were measured. The RBA values were calculated as for the rat uterine cytosol.

The RBA values are shown below in Table 1.

|  | Rat uterine cytosol | MCF-7 whole cells |
|---|---|---|
| Tamoxifen | 0.5–1.0 | 0.06 |
| 4-Hydroxytamoxifen | 100 | 2.9 |
| 4-Iodotamoxifen | 30 | 0.05 |
| 4-Bromotamoxifen | 3 | 0.02 |

The higher the values in the rat uterine cytosol test the greater the antiestrogenic effect. In the whole cell test, on the other hand, the estrogen receptors are localised in the cell nucleus and therefore bound to DNA. In the whole cell test, a low value indicating poor binding to cell nucleus ER and consequently low estrogenicity, can be considered favorable.

EXAMPLE 8

MCF-7 cells were grown as described in Example 7 and incubated at 37° C. for 24 hours with the test compound at three different concentrations. The test compounds according to the invention used were 3- and 4-iodotamoxifen 4- bromotamoxifen and the analogues of 4-iodotamoxifen in which the dimethylamino group is replaced by diethylamino and pyrrolidino (Examples 4 and 5 respectively). For comparison Z isomers of two of these compounds and tamoxifen itself were tested. Figures in Table 2 below give the percentage cell growth compared with a "blank" sample, and standard deviations obtained from figures for four separate samples of culture. Values greater than 100 indicate a growth stimulating (estrogenic) effect.

TABLE 2

| Test Compound (tamoxifen and derivatives and analogues thereof) | MCF-7 Cell Growth, % of Control Concentration of test compound | | |
|---|---|---|---|
| | $10^{-8}M$ | $10^{-7}M$ | $10^{-6}M$ |
| 4-Iodotamoxifen | 115 ± 6 | 42 ± 6 | 26 ± 2 |
| Z isomer of 4-iodotamoxifen (comparative) | 99 ± 13 | 126 ± 6 | 120 ± 3 |
| 3-Iodotamoxifen | 100 ± 8 | 68 ± 2 | 27 ± 5 |
| N,N—diethylamino analogue of 4-iodotamoxifen | 101 ± 7 | 35 ± 5 | 23 ± 2 |
| Pyrrolidino analogue of 4-iodotamoxifen | 84 ± 5 | 27 ± 3 | 20 ± 2 |
| 4-Bromotamoxifen | 130 ± 10 | 101 ± 8 | 63 ± 8 |
| Z isomer of 4-bromotamoxifen (comparative) | 110 ± 3 | 163 ± 4 | 174 ± 8 |
| TAMOXIFEN (comparative) | (not tested) | 52 ± 1 | 30 ± 1 |

It will be appreciated from Table 2 that $10^{-8}M$ was too low a concentration to differentiate the test compounds adequately and that $10^{-6}M$ was more realistic. The results indicate that the 4- iodo pyrrolidino derivative is particularly active, followed by the N,N-diethylamino derivative and the 4-iodo compound itself. The 3-iodo compound was about as active as tamoxifen in these tests, although the large deviation between individual results for this compound makes exact comparison difficult. The 4-bromo compound appeared less active than tamoxifen in these tests, in contrast to those of Example 7.

EXAMPLE 9

Following the procedure of Example 3 of U.S. Pat. No. 4,536,516 (ICI), 50 parts of 4-iodotamoxifen, 42 parts of maize starch and 7 parts of alginic acid are intimately mixed and granulated using 10% maize starch paste as the granulating agent. The granules are dried at a temperature not exceeding 50° C., and then mixed with 1 part of magnesium stearate and compressed into tablets each weighing 50 mg. There are thus obtained tablets suitable for oral administration for therapeutic purposes.

EXAMPLE 10

Preparation of 4-iodotamoxifen from 4-bromotamoxifen

This Example shows that 4-bromotamoxifen is readily convertible into 4-iodotamoxifen. The Example was carried out using ordinary ("cold", non-radioisotopic) molecular iodine, for reasons of laboratory safety but could obviously be repeated substituting a radioisotopic iodine for ordinary iodine.

To a stirred solution of E-1-[4-[2-dimethylamino)ethoxy]-1-(4-bromophenyl)-2-phenyl-1-butene (146.5 mg, 0.325 mmol) in tetrahydrofuran (1 ml) cooled to ca. −75° C. under an atmosphere of nitrogen was added a solution of tert-butyllithium in pentane (1.8M; 0.27 ml, 0.488 mmol). After 5 min, a solution of iodine (101.5 mg, 0.40 mmol) in tetrahydrofuran (1 ml) was added and the mixture allowed to warm to room temperature, then diluted with water (5 ml) and extracted with ether (2×5 ml). The ether solution was dried with sodium sulphate and concentrated. The residual oil was virtually entirely 4-iodotamoxifen by NMR. The product was recrystallized from light petroleum, b.p. 60°–80° C. Yield 108.6 mg, 67%, m.p. 110° C. (previously recorded m.p. 112°–114° C.).

Note that half of the iodine is lost as iodide by the reaction $Ar + I_2 \rightarrow ArI + I^-$ (where Ar represents the residue of the tamoxifen molecule). In a radiolabelled synthesis it would be advisable to add first a portion less than an equivalent and $I_2$ of radioisotopic iodine, then "cold" iodine to bring the reaction to completion.

EXAMPLE 11

Preparation of $^{125}I$ 4-iodotamoxifen from non-radioisotopic 4-iodotamoxifen 8 mg of "cold" 4-iodotamoxifen were dissolved in 1:1 ethanol-ethyl acetate. To this solution was added 25 μl of a solution prepared by dissolution of 12 mg copper (II) sulphate in 500 μl methanol, and also 5 μl of a solution of sodium iodide-125 (ca.100 μl Ci) in dilute sodium hydroxide. This mixture was heated for 1 h at 106°–107° C. in a 2 ml sealed vessel ("Reacti-vial"). Thin layer chromatography on silica gel (eluant 1:1 v/v ethanol-ethyl acetate or 4:4:1 v/v/v petroleum ether-diethyl ether-triethylamine) indicated more than 99% exchange labelling.

I claim:

1. 3- and 4-iodotamoxifen derivatives which are compounds of formula (3)

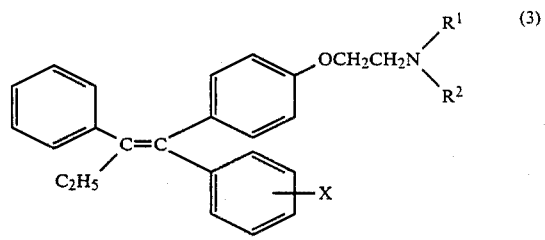

wherein X represents a 3- or 4- iodo substituent and $R^1$ and $R^2$, which may be the same or different, represent $C_{1-3}$ alkyl groups or $R^1$ represents a hydrogen atom and $R^2$ a $C_{1-3}$ alkyl group or $R^1$ and $R^2$ together with the nitrogen atom to which they are attached represent a saturated heterocyclic group and their pharmaceutically acceptable acid addition salts.

2. Iodotamoxifen derivatives according to claim 1 wherein $R^1$ and $R^2$ represent methyl groups or $R^1$ and $R^2$ together with the said nitrogen atom represent a pyrrolidino group.

3. Iodotamoxifen derivatives according to claim 2 wherein the iodo substituent is in the 4-position.

4. Iodotamoxifen derivatives according to claim 1, wherein the iodine atom is non-radioisotopic.

5. Iodotamoxifen derivatives acording to claim 2, wherein the iodine atom is non-radioisotopic.

6. Iodotamoxifen derivatives according to claim 3, wherein the iodine atom is non-radioisotopic.

7. A pharmaceutical composition comprising an iodotamoxifen derivative according to claim 1, in combination with a pharmaceutically effective diluent, carrier or excipient.

8. A method of treating an estrogen receptor-positive breast cancer in a human patient which comprises administering to the patient a therapeutically effective amount of a tamoxifen derivative according to claim 1.

9. A method of treating an estrogen receptor-positive breast cancer in a human patient which comprises administering to the patient a therapeutically effective amount of a tamoxifen derivative according to claim 4.

10. A method of detecting an estrogen receptor-positive breast cancer in a human ptient which comprises administering to the patient an effective amount of a tamoxifen derivative according to claim 1, wherein said iodine is a gammaray-emitting radioisotopic iodine atom and detecting the site at which the tamoxifen derivative binds to the estrogen receptor.

* * * * *